United States Patent [19]

Pollack

[11] Patent Number: 5,451,788
[45] Date of Patent: Sep. 19, 1995

[54] CHEMILUMINESCENT DETECTOR

[76] Inventor: Larry J. Pollack, 1550 Larimer St., No. 228, Denver, Colo. 80202-1602

[21] Appl. No.: 245,292

[22] Filed: May 18, 1994

[51] Int. Cl.⁶ .............................................. G01N 21/76
[52] U.S. Cl. .................................. 250/361 C; 422/52
[58] Field of Search ..................... 250/361 C; 422/52

[56] References Cited

U.S. PATENT DOCUMENTS

| | | | |
|---|---|---|---|
| 3,679,312 | 7/1972 | Mansberg | 250/361 C X |
| 3,763,877 | 10/1973 | Lieb | 137/117 |
| 3,856,473 | 12/1974 | Dillon | 23/254 E |
| 3,882,028 | 5/1975 | Zolner | 250/361 C |
| 3,963,928 | 6/1976 | Zolner | 250/361 C |
| 3,973,910 | 8/1976 | Fine | 23/230 |
| 3,998,592 | 12/1976 | Pyle | 250/361 C X |
| 4,301,114 | 11/1981 | Rounbehler et al. | 422/52 |
| 4,555,492 | 11/1985 | Spurlin et al. | 436/120 |
| 4,765,961 | 8/1988 | Schiff et al. | 422/52 |
| 5,227,135 | 7/1993 | Godec et al. | 422/98 |
| 5,250,259 | 10/1993 | Suda | 422/52 |
| 5,324,633 | 6/1994 | Fodor et al. | 422/52 X |

Primary Examiner—Constantine Hannaher
Assistant Examiner—Edward J. Glick
Attorney, Agent, or Firm—Duane, Morris & Heckscher

[57] ABSTRACT

A chemiluminescent detector having a first reflective layer; a second transparent layer; the first reflective layer having cut therein a first sample flow path; an exhaust flow path and a reagent flow path, said sample reagent and exhaust flow paths having at least one capillary channel joining the sample and reagent conduits such that the sample and reagent conduits can mix in the exhaust conduits at a plurality of discrete points and create a plurality of chemiluminescent reactions.

8 Claims, 8 Drawing Sheets

CHEMILUMINESCENT DETECTOR

FIELD OF THE INVENTION

The present invention is directed to chemiluminescent detectors. In particular, the present invention is directed to chemiluminescent detectors which are designed to be used with any sensor or photo multiplier tube (PMT).

BACKGROUND OF THE INVENTION

The present invention is directed to chemiluminescent reactions. Chemiluminescent reactions which occur between two chemicals or gases result in the emission of photons or light energy. In analytical instruments manufactured for monitoring gases, a common chemiluminescent devices titrate a reagent with a sample to form $NO_2$ plus energy (in the form of a light photon) and oxygen.

Chemiluminescence, under the right conditions, is an extremely sensitive method in both qualitative and quantitative determinations. The reactions from chemiluminescent reactions can correlate the emissions of photons with each molecule of interest, and thus can qualitatively and quantitatively determine for the presence of the molecule of interest at very low levels. Commonly, a typical reagent is the gas phase of ozone (atomic oxygen). Unfortunately, the reaction is not very selective and compounds like sulphur dioxide, nitrogen oxides and unsaturated hydrocarbons may produce emissions which can interfere with proper detection.

Because of efforts to reduce atmospheric pollution, reliable methods are needed for monitoring the level of various individual criteria gases from both the ambient atmosphere and various effluent sources, such as vehicle exhausts and the like. The detection of the presence of pollutants in part-per-million (PPM) levels by the observation of chemiluminescent reaction is particularly attractive because the method can be adapted to be continuous since long-length observation is not required, as in absorption spectroscopy. Traditional chemiluminescent detectors typically comprise a properly sized chamber where two gases, a sample and a reagent, are mixed uniformly so that virtually all of the NO is converted to $NO_2$. The resulting reaction produces a light photon which may be detected by a photo multiplier tube or solid state detector.

Such chambers are typically constructed with a window at one end so that a sensor, either a PMT (photo multiplier tube) or solid state detector, can register the level of light intensity resulting from the reaction (collision) of the gases.

While there are a number of chemiluminescent detectors, each share a number of common design considerations. First, the mixing of the two gases into the chamber must be turbulent so that the reaction is complete. The reaction must occur to close the window. It is assumed that the light distribution across the window is uniform, but it is usually a single spot.

The light generated from the reaction is diffuse in nature. The intensity of light decreases by a factor of the reciprocal of the distance from the excited molecules to the sensor squared. This principle is well known to those skilled in the art as the "Inverse Square Law". Because the chamber has a volume, the gain is dependent upon the design and typically is never fully optimized. To improve the chamber output, chambers are sometimes gold coated in order to improve their internal reflectance and thus the total light output. The response time of the analytical instrument is also effected by the volume of the chamber. The volume of the instrument should be kept low because the response time is generally important to users. Further, the materials used in constructing the chamber must be considered in the case where samples are corrosive so that the materials do not react with the sample or reaction by-product. The flow controls for the sample and reagent are external to the chamber.

The prior art is replete with examples of chemiluminescent detectors. None are directed to devices such as disclosed and claimed in the present invention. U.S. Pat. No. 4,555,491 discloses a reaction cell in which a quartz cell includes two quartz tubes which carry gas until they meet at a turbulence gap. An exit line permits the gases to be swept away for continuous monitoring. The device disclosed in this invention is typical of prior art devices in which a chemiluminescent reaction occurs at a single location or point on the detector.

U.S. Pat. No. 3,856,473 discloses a system in which optical chopping is utilized to modulate the luminescent signal into the A/C domain. The ozonator is energized periodically, e.g., in a pulsed mode.

U.S. Pat. No. 3,882,028 discloses apparatus adapted for measuring concentrations of constituents in a gas near ambient pressure by measuring the extent of chemiluminescent reaction which may occur in each of several small reaction chambers. In order to counteract the quenching effect associated with chemiluminescent reactions, and to promote more complete and rapid reactions in a reduced volume, each reaction chamber utilizes a concentric feed nozzle when an orifice is circumscribed by an opening for a second reactant such as ozone and in which the reactants are introduced at moderate pressure in intimate mixture into a relatively small reaction chamber.

U.S. Pat. No. 5,250,259 discloses a chemiluminescent detector which has an integral structure of the reaction unit and a detection unit. U.S. Pat. No. 3,963,928 discloses a signal processing means to demultiplex a light signal and to determine the relative concentration of constituents not directly observable by chemiluminescence or not distinguishable by observation.

U.S. Pat. No. 4,301,114 discloses a sieve trap which holds a number of packings. U.S. Pat. No. 4,765,961 similarly uses a system of traps instituting chemiluminescence reactions. Finally, U.S. Pat. No. 3,763,877 is directed to a fluid flow control system which maintains a constant fluid sample flow to a treating chamber.

Each of the prior art systems this facilitate chemiluminescent reactions by varying pressure or by eliminating noise or which create a reaction at a single location or point on the detector. While mass flow is a major issue, the control of flow has not heretofore been controlled in the detector. It would be desirable to provide a new design for a chemiluminescent detector constructed from micro-machine silicon and bonded to fused silica, quartz, glass, pyrex or any clear polymer. The surface of such a detector could comprise three major flow paths or conduits: a sample conduit, a reagent conduit and an exhaust conduit. The sample and reagent conduits would be coupled to the exhaust conduit through hundreds of smaller accurately machined capillaries. A pair of capillaries would direct the flow of sample and reagent at opposition into the exhaust path.

A reaction would occur at a plurality of collision points in the exhaust.

The present invention provides a number of advantages over systems associated with the prior art. First, the light distribution is uniform across the surface. Secondly, the reaction occurs at a uniform distance from the sensing device such as a PMT. With the device of the present invention, losses under the inverse square rule are uniform and predictable. The micro-machine silicon surface is reflective. Thus, even photons emitted 180° out of phase will be reflected back to sensor. Moreover, the detector material is not reactive with sample reagents. These and other objects and advantages of the present invention will become apparent from the following summary and detailed description which follows.

SUMMARY OF THE INVENTION

In accordance, a chemiluminescent detector comprises a reflective layer; a transparent layer, said reflective layer having a sample conduit, exhaust conduit and reagent conduits, said sample and reagent conduits being separated by said exhaust conduit and each of said sample and reagent conduits having at least one capillary channel which enters said exhaust such that the sample and reagent mix in the exhaust proximate to said capillary channels and initiate a chemiluminescent reaction.

In accordance with a more preferred embodiment of the present invention, a chemiluminescent detector comprising a first layer of reflective silicon; a second layer of transparent fused silica bonded to said silicon; a plurality of conduits etched into said silicon, said conduits comprising a sample conduit, reagent conduit for a reagent and an exhaust conduit interspersed between the reagent and sample conduits; and a plurality of capillaries for joining the sample and reagent conduits with the exhaust conduit such that the reagent and sample meet a number of locations in the exhaust conduit and thereby initiate a plurality of chemiluminescent reactions.

In yet a further embodiment, the present invention comprises a chemiluminescent detector comprising a first layer of silicon and second layer of fused silica, said layer of silicon being reflective, said layer of silicon having embedded therein a first fork-shaped conduit for carrying a reagent; a second fork-shaped conduit for carrying a sample extending in the direction opposite to said first fork-shaped conduit and being offset therefrom, the branches of the first and second fork-shaped conduits being intertwined; an exhaust conduit extending between said first and second conduits; and a plurality of capillaries between which link said first and second conduits with said exhaust.

In still yet another embodiment, the present invention is directed to a chemiluminescent detector comprising a first layer of silicon and second layer of fused silica, said first layer of silicon being reflective and having embedded therein a first fork-shaped conduit for carrying a reagent a second fork-shaped conduit for carrying a sample and extending in the direction opposite to said first fork-shaped conduit and being offset therefrom, the branches of said first and second fork-shaped conduits being intertwined; a serpentine exhaust conduit extending between the branches of said sample and reagent conduits; and a plurality of capillaries which link said sample and reagent conduits with said exhaust conduit so as to provide a plurality of sites on said exhaust conduit for chemiluminescent reactions.

DETAILED DESCRIPTION OF THE PRESENT INVENTION

Figure 1:
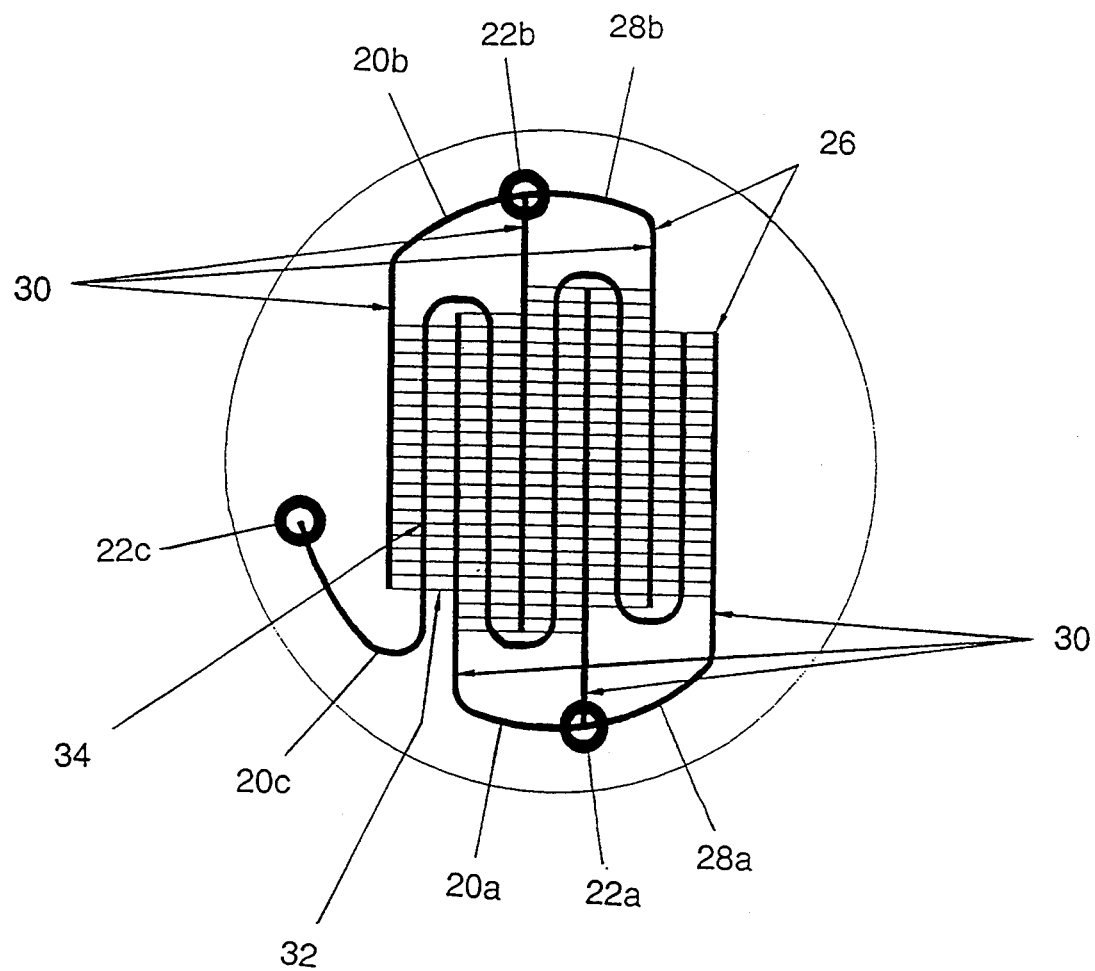
FIG. 1 is an overhead view of the chemiluminescent detector of the present invention.
Figure 2:
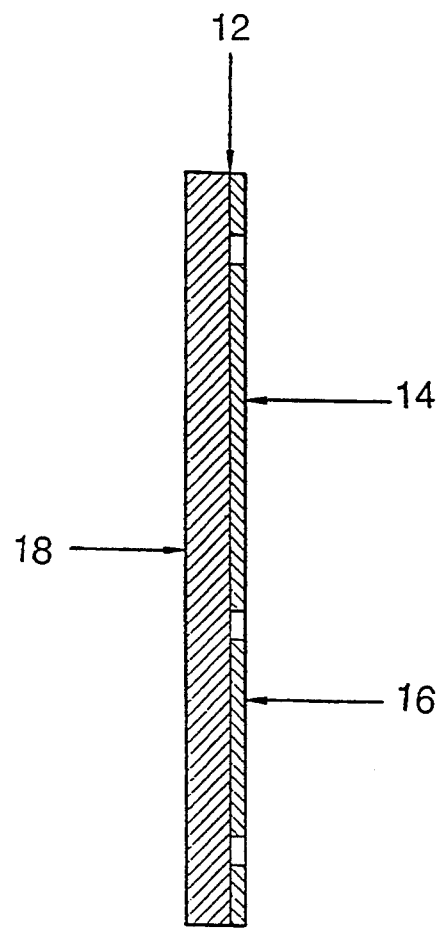
FIG. 2 is a side view of the chemiluminescent detector of the present invention along line 2—2 of FIG. 1.
Figure 4:
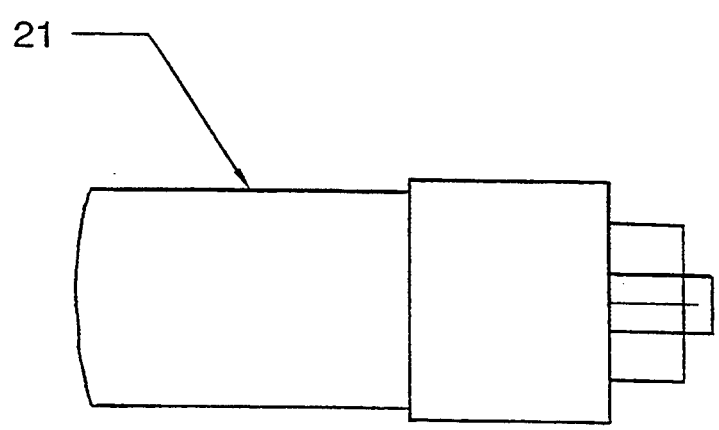
FIG. 4 is a perspective view of a photo multiplier tube to be used with the chemiluminescent detector of the present invention.

The present invention is described with reference to the enclosed Figures wherein the same numbers are utilized where applicable. Referring to FIGS. 1 and 2, the chemiluminescent detector 10 of the present invention is shown in a most preferred embodiment. The detector 10, in the most preferred embodiment, comprises a two layer bonded wafer structure 12 which is sandwiched. In a preferred embodiment, the first wafer layer 14 comprises a reflective mirror-like material, which in a preferred embodiment comprises a silicon surface 16. The reflective surface functions to reflect back photons which were emitted by the reaction of sample and reagent gases, to be described in detail below. The present invention is being described in the context of a silicon substrate. The material 16 can comprise any laser or mechanically etched material which may be reflective or be made reflective. The emitted photons are then amplified by a photomultiplier tube such as those manufactured by Burle (RCA), Hamamatsu, EMI, EG&G and Infrared Industries. The device can be used with both head-on PMT's 21 such as shown in FIG. 4 or side-on PMT's.

The second layer of the detector 10 comprises a layer of fused silica 18 and is bonded to the first silicon layer 16. The layer 18 may comprise other materials such as quartz, glass, pyrex or a clear polymer. The fused silica layer 18 is transparent to photons at relevant wavelengths and thus freely transmit photons and light energy at the relevant wavelengths. The detector 10, is shown as being comprised of two circular-shaped wafer members. It is to be appreciated that the detector 10 of the present invention may assume a variety of shapes and forms, other than a circular shape, such as a rectangular or ovular shape.

Figure 3:
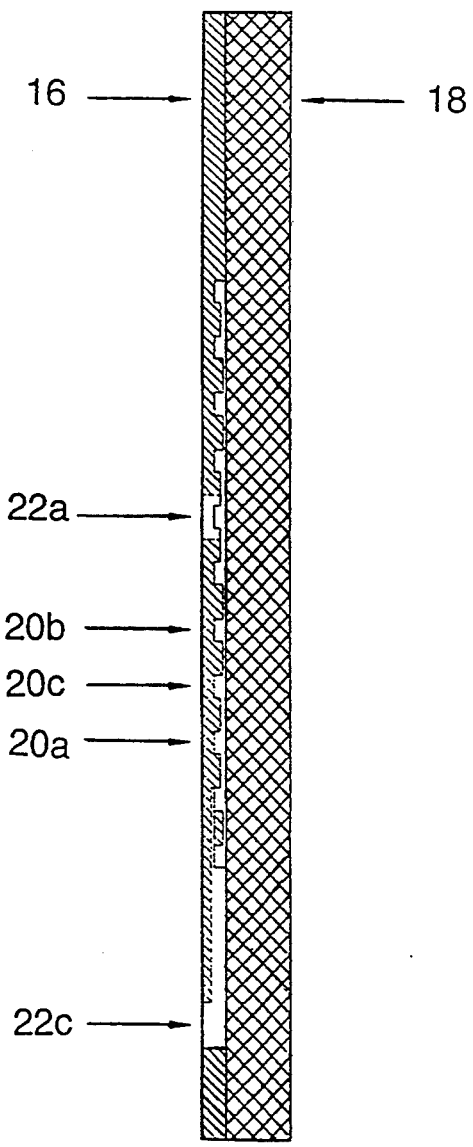
FIG. 3 is an enhanced section view of the chemiluminescent detector of the present invention along line 3—3 of FIG. 1.

As shown in FIGS. 1 and 3, the detector 10 contains three primary flow paths or conduits 20 which are preferably micro-machined into the layer of silicon 16. The conduits 20 comprise a reagent conduit 20a, a sample conduit 20b and an exhaust conduit 20c. Each of the conduits has an associated port 22a, 22b and 22c.

The reagent conduit 20a will typically carry a gas such as ozone ($O_3$), although any reagent will suffice in the present invention. The sample conduit 20b will carry a sample gas such as nitric oxide (NO). In the exhaust conduit 20c, the sample and reagent gases mix to form nitrous oxide ($NO_2$), oxygen and energy in the form of a photon (light) which will be emitted.

As shown in the first embodiment of FIGS. 1 through 3, the sample conduits and reagent conduits form interlocked oppositely disposed fork-shaped conduits 20a, 20b which are vertically offset 26 from each other. Each of these conduits 20a, 20b comprises a cross-piece 28a, 28b centered about a port 22a, 22b, 22c and a plurality of prong-shaped arm conduits 30. As shown in the first embodiment, the exhaust conduit 20c flows in a serpentine fashion between the interlocked arms 30 of the fork-shaped members of the sample and reagent conduits 20a, 20b.

A key feature of the present invention is the inclusion of a plurality of micro-machine capillaries 32 which permit the flow of sample and reagent into discrete portions of the exhaust conduit 20c at the points where the sample and reagent capillaries 32 meet the exhaust conduit 20c. Because chemiluminescent reactions are mass flow based, the capillaries control the molecular flow. In a preferred embodiment, the capillaries are machined into the silicon 16. Alternatively, the capillaries 32 may be machined into the fused silica layer 18.

Figure 6:
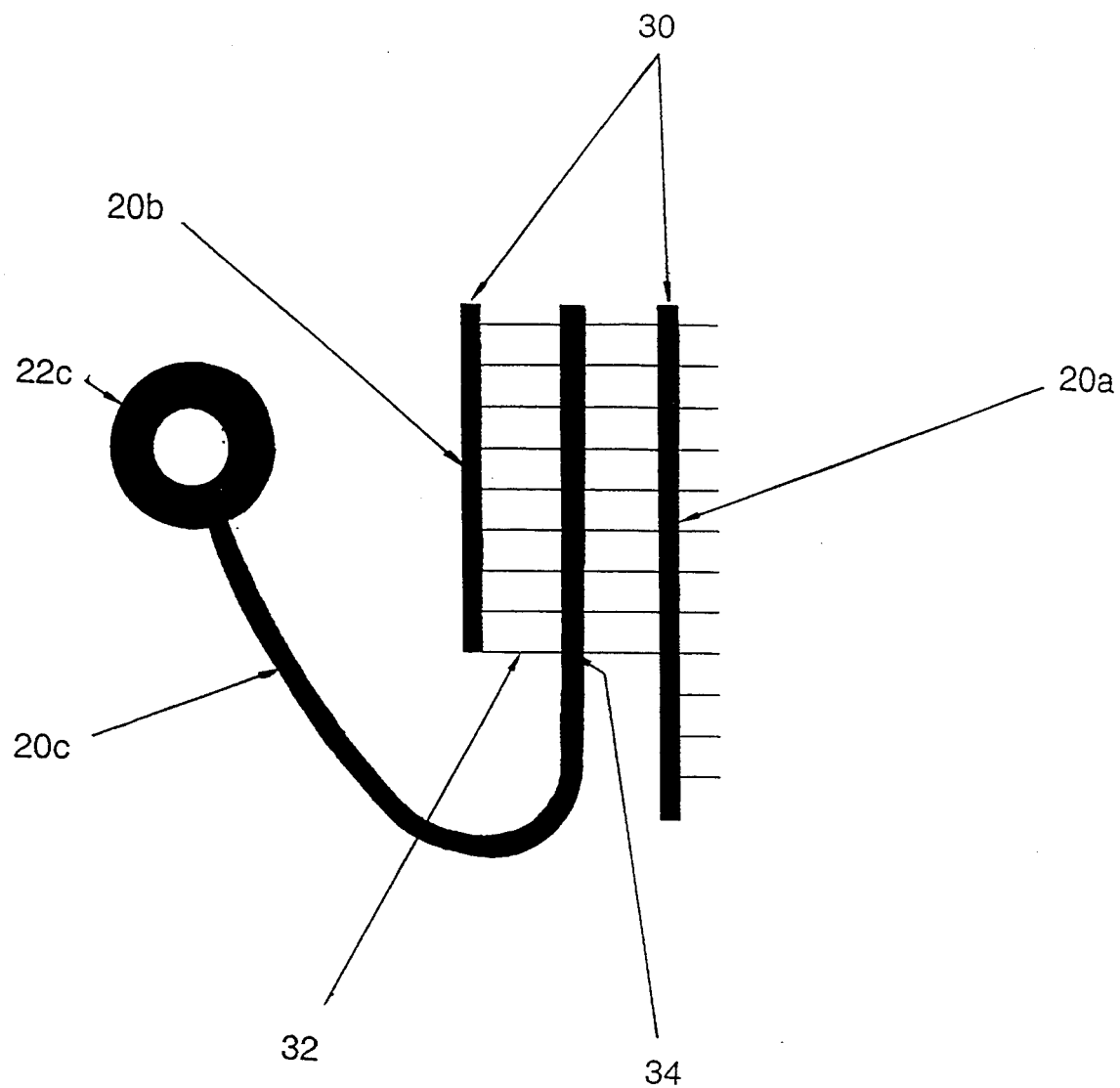
FIG. 6 is an exploded view of the junction point, the capillaries and exhaust conduit.

As shown most particularly in FIG. 6, the reagent and sample gases thus mix across the surface of the exhaust conduit 20C at each point 34 where the capillaries from the reagent and sample conduit 20, 20b converge. The reaction and the emission of photons or light is thereby evenly released and dispersed across the exhaust conduit at each point 34. Because the flow area of the exhaust conduit 20c is very small, photons are reflected by the reflective silicon 16 with very little loss. Even if the photon is emitted 180° out of phase with the silica, it will be reflected back by the silicon layer 16 with minimal loss and will be amplified by the PMT.

Figure 5A:
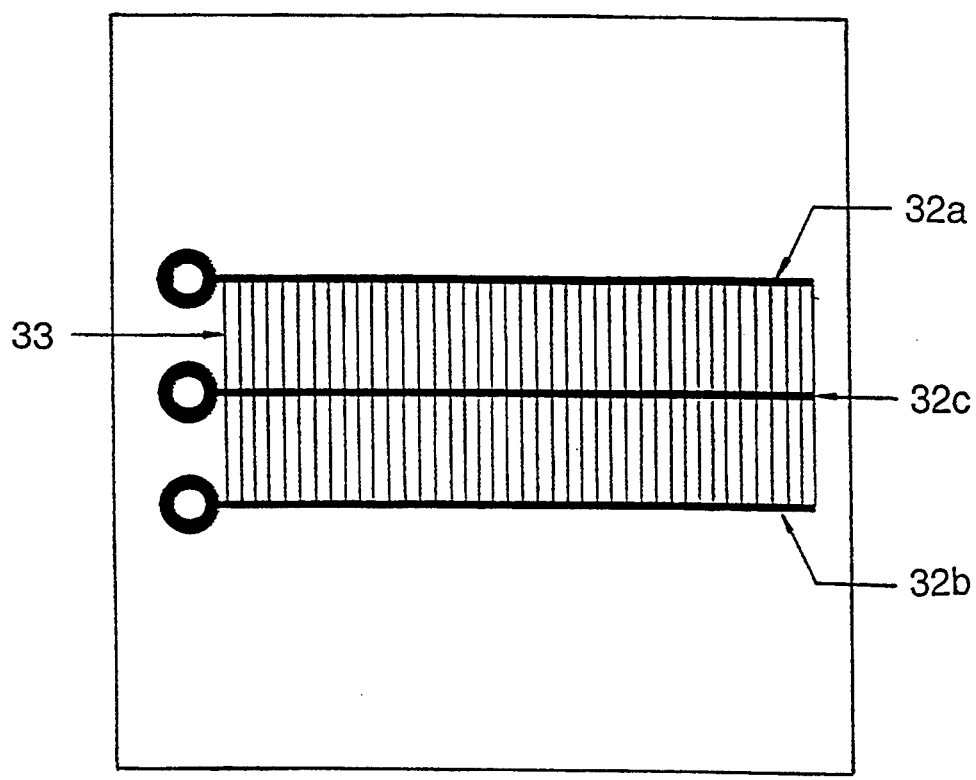
FIGS. 5A–5C are overhead views of alternative embodiments of the present invention.

While the present has been shown in the context of a device having interlocking fork-shaped flow conduits, it is to be appreciated that a number of alternative embodiments are suggested by the present invention. As shown in FIG. 5A, a first alternative embodiment comprises an embodiment having straight reagent, sample and exhaust conduits 32a, 32b, 32c. In this example, the capillaries 33 extend between the parallel sample and reagent conduits and the exhaust conduit and initiate a reaction at a plurality of discrete points 34 where the capillaries 33 meet the exhaust conduit 32c.

Figure 5B:
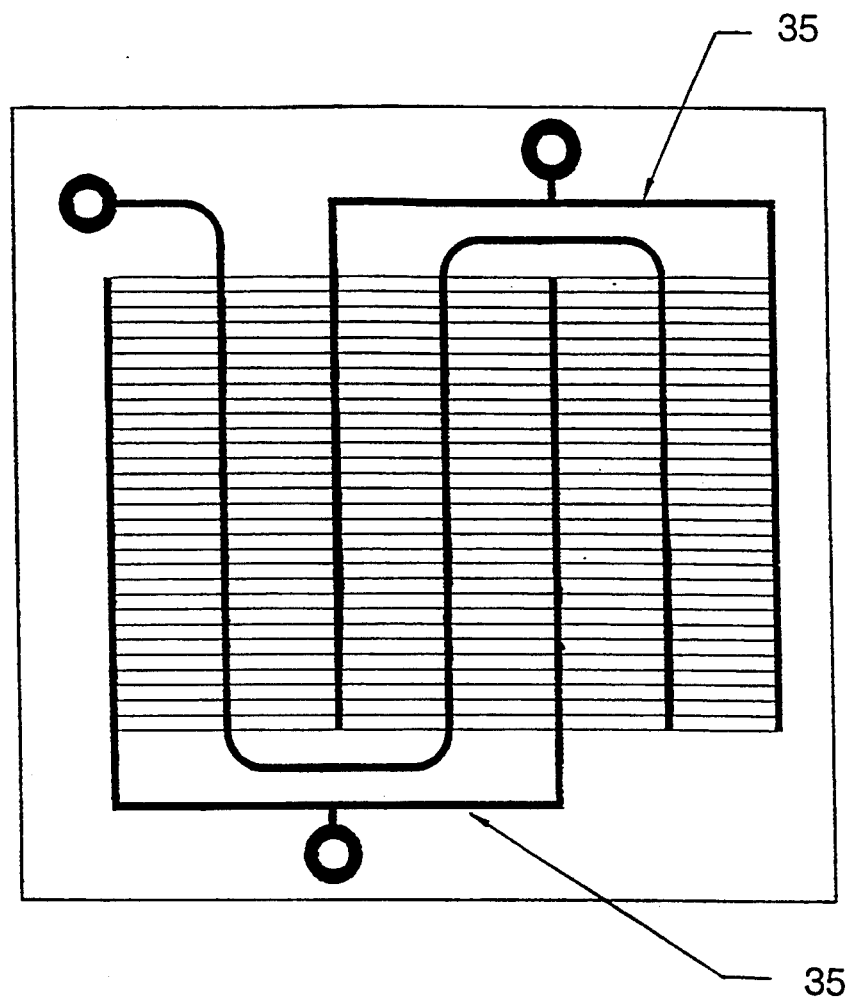

Further, as shown in FIG. 5B, the present invention can further be utilized with a fork-shaped conduit structure which includes less than two prongs on each of the forks of the reagent and sample conduits. FIG. 5B illustrates an example in which there are interlocked two pronged fork-shaped conduits 35.

Figure 5C:
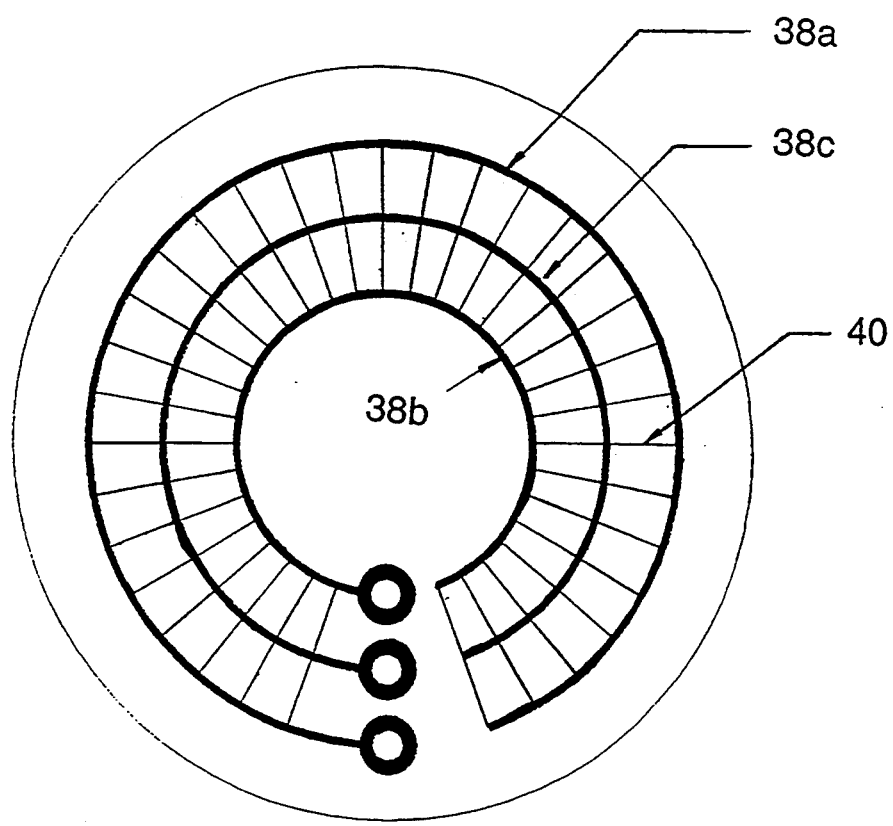

FIG. 5C illustrates an embodiment having a ring-like configuration 36. In this embodiment, the exhaust conduit forms a central ring 38c which joins the sample and reagent conduits 38a, 38b through a plurality of radially extending capillaries 40. As with the previously discussed embodiments, a plurality of chemiluminescent reactions occur at the junctions of the ring-shaped exhaust conduit and capillaries. Still further embodiments are suggested by the present invention.

It is to be noted that a key feature of the present invention is the inclusion of the pairs of micro-machine capillaries which direct the flow of sample and reagent at opposition into the exhaust conduit. With the use of the capillary structure of the present invention, the mixing of sample and reagent occurs at a number sites across the surface of the detector. The light distribution resulting therefrom is accordingly equally dispersed across the surface of the detector.

The present invention has been described with reference to the enclosed Figures. It is to be appreciated that other embodiments fulfill the spirit and scope of the present invention and that the true nature and scope of the present invention is to be determined with reference to the claims appended hereto.

What is claimed is:

1. A chemiluminescent detector comprises:
   a reflective layer;
   a transparent layer,
   said reflective layer having a sample conduit, exhaust conduit and reagent conduits, said sample and reagent conduits being separated by said exhaust conduit and each of said sample and reagent conduits having at least one capillary channel which enters said exhaust conduit such that the sample and reagent mix in the exhaust conduit proximate to said capillary channels and initiate a chemiluminescent reaction.

2. The chemiluminescent detector of claim 1 wherein said reflective layer comprises silicon.

3. The chemiluminescent detector of claim 1 wherein said transparent layer comprises fused silica.

4. A chemiluminescent detector comprising:
   a first layer of reflective silicon;
   a second layer of transparent fused silica bonded to said silicon;
   a plurality of conduits embedded into said silicon, said conduits comprising a sample conduit, reagent conduit for a reagent and
   an exhaust conduit interspersed between the reagent and sample conduits; and
   a plurality of capillaries for joining the sample and reagent conduits with the exhaust conduit such that the reagent and sample meet a number of locations in the exhaust conduit and thereby initiate a plurality of chemiluminescent reactions.

5. The chemiluminescent detector of claim 4 wherein said detector has a circular shape.

6. The chemiluminescent detector of claim 4 wherein said sample and reagent conduits comprise interlocked fork-shaped conduit members.

7. The chemiluminescent detector of claim 4 wherein said exhaust conduit comprises a serpentine-shaped conduit which is interspersed between the prongs of the fork-shaped sample and reagent conduits.

8. A chemiluminescent detector comprising:
   a first layer of silicon and second layer of fused silica, said first layer of silicon being reflective and having embedded therein: a first fork-shaped conduit for carrying a reagent; a second fork-shaped conduit for carrying a sample, said second fork-shaped conduit extending in a direction opposite to said first fork-shaped conduit and being offset therefrom, the branches of said first and second fork-shaped conduits being intertwined;
   a serpentine exhaust conduit extending between the branches of said sample and reagent conduits; and
   a plurality of capillaries which link said sample and reagent conduits with said exhaust conduit so as to provide a plurality of sites on said exhaust conduit for chemiluminescent reactions.

* * * * *